United States Patent [19]

Fried

[11] Patent Number: 5,753,637
[45] Date of Patent: May 19, 1998

[54] METHOD OF TREATING ACNE CONDITIONS

[75] Inventor: Karen G. Fried, Raritan Township, Hunterdon County, N.J.

[73] Assignee: Ideal Ideas, Inc., Flemington, N.J.

[21] Appl. No.: 780,211

[22] Filed: Jan. 8, 1997

Related U.S. Application Data

[63] Continuation-in-part of Ser. No. 728,546, Oct. 9, 1996.
[51] Int. Cl.⁶ .......... A61K 31/44; A61K 31/62; A61K 31/605; A61K 33/32
[52] U.S. Cl. .......... 514/161; 424/642; 514/164; 514/355; 514/714
[58] Field of Search .......... 514/714, 161, 514/164, 355; 424/642

[56] References Cited

U.S. PATENT DOCUMENTS

| | | | |
|---|---|---|---|
| 4,536,399 | 8/1985 | Flynn et al. | 514/63 |
| 4,670,185 | 6/1987 | Fujiwara et al. | 252/311 |
| 4,923,900 | 5/1990 | De Villez | 514/714 |
| 4,978,332 | 12/1990 | Luck et al. | 604/19 |
| 5,086,075 | 2/1992 | De Villez | 514/714 |
| 5,466,446 | 11/1995 | Stiefel et al. | 514/714 |
| 5,470,884 | 11/1995 | Corless et al. | 514/714 |

FOREIGN PATENT DOCUMENTS

84/02845  8/1984  WIPO.

*Primary Examiner*—Allen J. Robinson
*Attorney, Agent, or Firm*—Kenneth P. Glynn, Esq

[57] ABSTRACT

The acne treatment method of the present invention includes applying to skin a composition including an effective amount of acne treatment medication selected from the group consisting of benzoyl peroxide and salicylic acid, an effective amount of a vasoconstrictor and an inert carrier. The acne treatment medication is therapeutic to acne conditions by acting as an antibacterial agent. The vasoconstrictor removes the redness normally associated with acne conditions as well as additional redness which may be caused by the benzoyl peroxide itself. The carrier is simply an inert flowing carrier to permit the application of the active ingredients to the skin. In preferred embodiments about 1 to 15% of the acne treatment medication based on the total weight of the composition is included. The preferred acne treatment medication is benzoyl peroxide and the preferred vasoconstrictor is tetrahydrozoline hydrochloride or a combination of tetrahydrozoline hydrochloride and zinc sulfate.

17 Claims, No Drawings

METHOD OF TREATING ACNE CONDITIONS

REFERENCE TO RELATED APPLICATION

This application is a continuation-in-part of copending U.S. patent application filed on Oct. 9, 1996, Ser. No. 08/728,546, by the same inventor herein and entitled, "Acne Treatment Composition with Vasoconstrictor", now pending.)

BACKGROUND OF THE INVENTION

1. Field of the Invention

The present invention relates to a method of treating acne conditions using an acne treatment composition which provides for the treatment of acne conditions (decreases pimple duration or incidence) while rapidly removing redness which is normally manifested with acne conditions.

2. Information Disclosure Statement

The following patents represent compositions and formulation prior art utilizing either acne treatments or vasoconstrictors, but none teach or suggest the combination of both in a method:

U.S. Pat. No. 5,470,884 relates to anti-acne compositions having good efficacy, low skin irritation, and good physical and chemical stability. These compositions comprise a benzoyl peroxide, a wetting agent, water, a non-volatile emollient component which is a liquid at 25° C. and which has a weighted arithmetic mean solubility parameter of less than or equal to about 7, and a water soluble or dispersible gelling agent.

U.S. Pat. No. 5,466,446 relates to dermatological conditions that are treated by topically applying to the affected area an effective amount of a combination benzoyl peroxide and clindamycin composition.

U.S. Pat. No. 5,086,075 is directed to a stable composition and method for cutaneous therapy, particularly for treatment of acne, dermatophyte infection, poison ivy reactions and body odor development. The composition includes benzoyl peroxide particles, water and a solvent for benzoyl peroxide which has a boiling point substantially greater than 100° C. Evaporation of the water leaves a solvent-benzoyl peroxide solution particularly non-irritative and effective in activity against cutaneously abiding microorganisms and contactants characteristic of certain plants.

U.S. Pat. No. 4,978,332 relates to a pharmaceutical composition and method of treating cellular disorders involving abnormal solid cellular growths which comprises administering a pharmaceutical composition containing cytotoxic agents in combination with a vasoconstrictive drug. Enhanced effectiveness of the composition is observed, with reduced cytotoxic effects on cells distant from the site of introduction. Agents may be included to enhance therapeutic gain and reduce adverse affects to normal tissue.

U.S. Pat. No. 4,923,900 is directed to a stable composition and method for cutaneous therapy, particularly for treatment of acne, dermatophyte infection, poison ivy reactions and body odor development. The composition includes benzoyl peroxide particles, water and a solvent for benzoyl peroxide which has a boiling point substantially greater than 100° C. Evaporation of the water leaves a solvent-benzoyl peroxide solution particularly non-irrative and effective in activity against cutaneously abiding microorganisms and contactants characteristics of certain plants.

Notwithstanding the prior art, the present invention is neither taught nor rendered obvious thereby.

SUMMARY OF THE INVENTION

The method of treating acne conditions of the present invention includes applying an effective amount of acne treatment composition to an acne problem area. The acne treatment composition includes an effective amount of an acne treatment medication selected from the group consisting of benzoyl peroxide and salicylic acid, an effective amount of a vasoconstrictor and an inert carrier. The acne treatment medication is therapeutic to acne conditions by acting as an antibacterial agent. The vasoconstrictor removes the redness normally associated with acne conditions, as well as additional redness which may be caused by the acne treatment medication itself. The carrier is simply an inert flowing carrier to permit application of the active ingredients to the skin. In preferred embodiments, about 1 to 15% of the acne treatment medication based on the total weight of the composition is included. The preferred acne treatment medication is benzoyl peroxide and the preferred vasoconstrictor is tetrahydrozoline hydrochloride or a combination of tetrahydrozoline hydrochloride and zinc sulfate.

DETAILED DESCRIPTION OF THE PRESENT INVENTION

In the present invention, an effective amount of acne treatment composition is applied to skin. The acne treatment composition includes an effective amount of acne treatment medication, an effective amount of vasoconstrictor and an inert carrier. The acne treatment medicine used in the composition which is applied is selected from the group consisting of benzoyl peroxide and salicylic acid. With regard to the benzoyl peroxide, it is utilized in the present invention in an amount of at least about 0.1% up to 20%. In a preferred embodiment, at least about 1.0% up to 15% of benzoyl peroxide is included in the composition based on total weight of the composition. With respect to the salicylic acid, it utilized in an amount of at least 0.05% by weight up to about 15% by weight, based on the total weight of the composition, and preferably, at least about 0.1% up to about 10% by weight.

The vasoconstrictor used in the composition of the present invention method is used in an amount of about 0.01% up to about 20%, and preferably about 0.1% to about 10%, by weight based on the total weight of the composition. The vasoconstrictor used in the present invention functions to remove the redness from the acne problem areas of the skin. Such vasoconstrictors include catecholamines, norepinephrine, epinephrine, isoproterenol, dopamine, ephedrine, phenylisopropylamines, phenylephrine, amphetamine, metraminol, methoxamine, lysergic acid, lysergic acid diethylamine, and other known vasoconstrictors. The preferred vasoconstrictor is tetrahydrozoline hydrochloride, and tetrahydrozoline hydrochloride with zinc sulfate.

The inert carriers in the composition which is applied may be in the form of a solution, emulsion, dispersion, gel, lotion or cream. Such inert carriers are common for acne treatment compositions and are well known by the artisan. Such carriers may be water-based or organically based, but most commercial inert carriers for acne medication contain both organic materials and water or purified water.

Examples of inert carriers for the purpose of the present invention include mixtures of water, glycerine, aloe vera gel and pigmentations. Others include various oils such as castor oil, butyl paraben, ethyl paraben, propyl paraben, cetyl alcohol, and polyethylene glycols. Yet others may include petrolatum, or mixtures diisopropanolamine, polycarbonates and purified water. Such inert carriers may include pigmentation and other inert materials to enhance the feel, look, or aroma of the solution and these, too, one well known in the field. Particular blends of carriers are not critical to the present invention, as long as they provide no interference with the activity of the acne treatment medication and the vasoconstrictor, and hence, are inert. Additionally, they must also provide no toxicology or acceptability problems when applied to the skin and provide adequate viscosity to prevent running.

The present invention method applies the compositions by spreading them on an acne problem area, sufficiently to cover the area to be treated.

EXAMPLES

Acne treatment compositions of the present invention are prepared by blending various levels of an active acne treatment medication with an active vasoconstrictor component and an inert carrier. The following Examples are presented for illustration and the present invention should not be construed as being limited thereto:

EXAMPLE 1

|  | wt % of total wt |
| --- | --- |
| Acne treatment medication: |  |
| benzoyl peroxide | 2.5% |
| Vasoconstrictor: |  |
| tetrahydrozoline hydrochloride | 0.05% |
| Inert Carrier: |  |
| aloe vera gel | 97.45% |

EXAMPLE 2

|  | wt % of total wt |
| --- | --- |
| Acne treatment medication: |  |
| benzoyl peroxide | 5.0% |
| Vasoconstrictor: |  |
| tetrahydrozoline hydrochloride | 0.1 |
| Inert carrier: |  |
| purified water | 25.0% |
| diazolidinyl urea | 20.0% |
| glycerine | 20.0% |
| propylene glycol | 20.0% |
| sodium hydroxide | 8.0% |
| silica | 1.9% |

EXAMPLE 3

|  | wt % of total wt |
| --- | --- |
| Acne treatment medication: |  |
| salicylic acid | 2.0% |
| Vasoconstrictor: |  |
| tetrahydrozoline hydrochloride | 0.05% |
| zinc sulfate | 0.25% |

-continued

|  | wt % of total wt |
| --- | --- |
| Inert carrier: |  |
| purified water | 15.0% |
| glycerine | 37.0% |
| propylene glycol | 35.0% |
| sodium hydroxide | 7.5% |
| silica | 2.2% |

EXAMPLE 4

|  | wt % of total wt |
| --- | --- |
| Acne treatment medication: |  |
| benzoyl peroxide | 10.0% |
| Vasoconstrictor: |  |
| tetrahydrozoline hydrochloride | 0.05% |
| zinc sulfate | 0.30% |
| Inert carriers: |  |
| aloe vera gel | 89.65% |

EXAMPLE 5

|  | wt % of total wt |
| --- | --- |
| Acne treatment medication: |  |
| benzoyl peroxide | 5.0% |
| Vasoconstrictor: |  |
| lysergic acid | 1.5% |
| Inert carriers: |  |
| purified water | 25.0% |
| diazolidinyl urea | 20.0% |
| glycerine | 18.5% |
| propylene glycol | 20.0% |
| sodium hydroxide | 8.0% |
| silica | 2.0% |

EXAMPLE 6

|  | wt % of total wt |
| --- | --- |
| Acne treatment medication: |  |
| benzoyl peroxide | 6.0% |
| Vasoconstrictor: |  |
| tetrahydrozoline hydrochloride | 0.4% |
| zinc sulfate | 0.2% |
| Inert carriers: |  |
| purified water | 15.0% |
| acrylate copolymers | 16.0% |
| diazolidinyl urea | 20.0% |
| glycerine | 18.5% |
| propylene glycol | 10.0% |
| sodium hydroxide | 8.0% |
| silica | 2.0% |
| citric acid | 0.8% |
| xanthan gum | 1.1% |
| sodium citrate | 2.0% |

EXAMPLE 7

Two samples of approximately 3 mg of the composition preparation in accordance with EXAMPLE 3 were applied to acne areas of the face and the redness and swelling was substantially reduced within five minutes.

EXAMPLE 8

Six samples of the composition prepared in accordance with EXAMPLE 5 were applied to human skin on the underside forearm area to test for allergic reactions. None were experienced or observed.

EXAMPLE 9

Samples of the composition prepared in accordance with EXAMPLE 5 above were applied to two separate acne problem areas on the face. In both cases the acne treatment medication acted to eliminate the pimple problem and the vasoconstrictor removed the redness around the pimple immediately. The redness never returned and the pimple healed.

Obviously, numerous modifications and variations of the present invention are possible in light of the above teachings. It is therefore understood that within the scope of the appended claims, the invention may be practiced otherwise than as specifically described herein.

What is claimed is:

1. A method of treating acne conditions, which comprises:
    applying to an acne problem area an effective enhanced amounts of an acne treatment composition to treat acne, which composition includes:
        (a) an acne treatment medication selected from the group consisting of benzoyl peroxide and salicylic acid;
        (b) the vasoconstrictor tetrahydrozoline hydrochloride and optionally zinc sulfate and,
        (c) an inert carrier.

2. The method of claim 1, wherein said acne treatment medication is benzoyl peroxide.

3. The method of claim 2 wherein said benzoyl peroxide is in an amount of about 0.1% to about 20% by total weight of the composition.

4. The method of claim 3 wherein said benzoyl peroxide is in an amount of about 1.0% to about 15% by total weight of the composition.

5. The method of claim 1 wherein said acne treatment medicine is salicylic acid.

6. The method of claim 5 wherein said salicylic acid is in an amount of 0.05% to 15.0% by total weight of the composition.

7. The method of claim 6 wherein said salicylic acid is in an amount of about 0.1% to 10.0% by total weight of the composition.

8. The method of claim 1 wherein said tetrahydrozoline hydrochloride is in an amount of about 0.01% to about 20% by weight, based on the total weight of the composition.

9. The method of claim 8 wherein said tetrahydrozoline hydrochloride is in a preferred amount of about 0.1% to about 10% by weight, based on the total weight of the composition.

10. The method of claim 1 wherein said vasoconstrictor consists of a combination of tetrahydrozoline hydrochloride and zinc sulfate.

11. The method of claim 2 wherein said vasoconstrictor consists of a combination of tetrahydrozoline hydrochloride and zinc sulfate.

12. The method of claim 3 wherein said vasoconstrictor consists of a combination of tetrahydrozoline hydrochloride and zinc sulfate.

13. The method of claim 4 wherein said vasoconstrictor consists of a combination of tetrahydrozoline hydrochloride and zinc sulfate.

14. The method of claim 5 wherein said vasoconstrictor consists of a combination of tetrahydrozoline hydrochloride and zinc sulfate.

15. The method of claim 6 wherein said vasoconstrictor consists of a combination of tetrahydrozoline hydrochloride and zinc sulfate.

16. The method of claim 7 wherein said vasoconstrictor consists of a combination of tetrahydrozoline hydrochloride and zinc sulfate.

17. The method of claim 1 wherein said carrier is a spreadable carrier.

* * * * *